(12) United States Patent
Marvel

(10) Patent No.: US 8,764,829 B2
(45) Date of Patent: *Jul. 1, 2014

(54) BUFFER FOR A HUMAN JOINT AND METHOD OF ARTHROSCOPICALLY INSERTING

(76) Inventor: James Marvel, Mineola, TX (US)

( * ) Notice: Subject to any disclaimer, the term of this patent is extended or adjusted under 35 U.S.C. 154(b) by 30 days.

This patent is subject to a terminal disclaimer.

(21) Appl. No.: 13/179,869

(22) Filed: Jul. 11, 2011

(65) Prior Publication Data

US 2011/0270393 A1 Nov. 3, 2011

Related U.S. Application Data

(63) Continuation of application No. 12/133,211, filed on Jun. 4, 2008, now Pat. No. 7,976,578.

(51) Int. Cl.
*A61F 2/08* (2006.01)

(52) U.S. Cl.
USPC .................................................. 623/14.12

(58) Field of Classification Search
USPC .......... 623/17.15, 17.16, 14.12; 606/247, 249
See application file for complete search history.

(56) References Cited

U.S. PATENT DOCUMENTS

| | | | | |
|---|---|---|---|---|
| 4,166,292 A * | 9/1979 | Bokros | ...................... | 623/21.18 |
| 4,502,161 A * | 3/1985 | Wall | ............................. | 623/14.12 |
| 4,863,477 A * | 9/1989 | Monson | ..................... | 623/17.12 |
| 4,919,667 A * | 4/1990 | Richmond | ................. | 623/14.12 |
| 4,919,668 A * | 4/1990 | Rosenbaum et al. | ...... | 623/17.17 |
| 4,932,969 A * | 6/1990 | Frey et al. | .................. | 623/17.12 |
| 5,344,459 A * | 9/1994 | Swartz | ........................ | 623/14.12 |
| 5,549,679 A * | 8/1996 | Kuslich | ....................... | 623/17.12 |
| 5,593,445 A * | 1/1997 | Waits | .......................... | 623/23.42 |
| 5,674,296 A * | 10/1997 | Bryan et al. | ............... | 623/17.16 |
| 5,893,889 A * | 4/1999 | Harrington | ............... | 623/17.16 |
| 6,022,376 A * | 2/2000 | Assell et al. | ............... | 623/17.16 |
| 6,206,927 B1 * | 3/2001 | Fell et al. | ................... | 623/20.29 |
| 6,248,131 B1 * | 6/2001 | Felt et al. | .................... | 623/17.12 |
| 6,419,704 B1 * | 7/2002 | Ferree | ........................ | 623/17.12 |
| 6,482,234 B1 * | 11/2002 | Weber et al. | ............... | 623/17.12 |
| 6,527,804 B1 * | 3/2003 | Gauchet et al. | ............ | 623/17.12 |
| 6,582,466 B1 * | 6/2003 | Gauchet | ..................... | 623/17.11 |
| 6,629,997 B2 * | 10/2003 | Mansmann | ................ | 623/14.12 |
| 6,632,235 B2 * | 10/2003 | Weikel et al. | ................ | 606/192 |
| 6,679,914 B1 * | 1/2004 | Gabbay | ...................... | 623/14.12 |
| 6,682,562 B2 * | 1/2004 | Viart et al. | ................. | 623/17.14 |
| 6,733,532 B1 * | 5/2004 | Gauchet et al. | ............ | 623/17.12 |
| 6,733,533 B1 * | 5/2004 | Lozier | ........................ | 623/17.12 |
| 6,893,465 B2 * | 5/2005 | Huang | ........................ | 623/17.12 |
| 6,984,246 B2 * | 1/2006 | Huang | ........................ | 623/17.13 |
| 7,001,431 B2 * | 2/2006 | Bao et al. | ................... | 623/17.12 |

(Continued)

*Primary Examiner* — Alvin Stewart
(74) *Attorney, Agent, or Firm* — Hovey Williams LLP

(57) ABSTRACT

A buffer (10) for placement in a human knee between the femur and tibia comprises an outer sack (14) formed of a pliable material and having a one-way valve (22), a generally circularly shaped inner ring (16) received within the outer sack (14), and a friction reducing fluid (18) received within the outer sack (14) via the one-way valve (22). The inner ring (16) includes top and bottom surfaces (38,40) angled inwardly with respect to each other, such that the ring (16) is generally concave. The buffer (10) is configured for insertion between the femur and tibia so as to at least partially prevent the bones from contacting each other, which reduces the pain and discomfort associated with a loss of articular cartilage (12). The buffer (10) is arthroscopically inserted in the knee using an especially designed sleeve (20) configured for support of the buffer (10) during insertion.

13 Claims, 3 Drawing Sheets

(56) References Cited

U.S. PATENT DOCUMENTS

| | | | |
|---|---|---|---|
| 7,004,971 B2* | 2/2006 | Serhan et al. | 623/17.16 |
| 7,244,273 B2* | 7/2007 | Pedersen et al. | 623/14.12 |
| 7,250,060 B2* | 7/2007 | Trieu | 623/17.15 |
| 7,297,161 B2* | 11/2007 | Fell | 623/14.12 |
| 7,485,145 B2* | 2/2009 | Purcell | 623/17.12 |
| 7,527,647 B2* | 5/2009 | Spence | 623/2.36 |
| 7,534,268 B2* | 5/2009 | Hudgins et al. | 623/17.12 |
| 7,618,457 B2* | 11/2009 | Hudgins | 623/17.12 |
| 7,641,691 B2* | 1/2010 | Lotz et al. | 623/17.12 |
| 7,645,301 B2* | 1/2010 | Hudgins et al. | 623/17.12 |
| 7,708,777 B2* | 5/2010 | O'Neil et al. | 623/17.14 |
| 7,744,630 B2* | 6/2010 | Lancial | 606/247 |
| 7,799,079 B2* | 9/2010 | Hestad et al. | 623/17.12 |
| 7,803,193 B2* | 9/2010 | Steinberg | 623/20.21 |
| 7,819,919 B2* | 10/2010 | Fell | 623/14.12 |
| 7,824,444 B2* | 11/2010 | Biscup et al. | 623/17.12 |
| 7,837,739 B2* | 11/2010 | Ogilvie | 623/21.15 |
| 7,842,088 B2* | 11/2010 | Rashbaum et al. | 623/17.15 |
| 7,927,374 B2* | 4/2011 | Duggal et al. | 623/17.14 |
| 7,976,578 B2* | 7/2011 | Marvel | 623/14.12 |
| 8,034,080 B2* | 10/2011 | Malandain et al. | 606/249 |
| 8,038,698 B2* | 10/2011 | Edidin et al. | 606/246 |
| 8,057,547 B2* | 11/2011 | Hurlbert et al. | 623/17.14 |
| 8,062,375 B2* | 11/2011 | Glerum et al. | 623/17.16 |
| 8,100,964 B2* | 1/2012 | Spence | 623/2.36 |
| 8,147,517 B2* | 4/2012 | Trieu et al. | 606/248 |
| 8,147,526 B2* | 4/2012 | Auyoung | 606/279 |
| 8,202,320 B2* | 6/2012 | Burgess et al. | 623/17.14 |
| 8,206,439 B2* | 6/2012 | Gomez Duran | 623/2.37 |
| 8,211,175 B2* | 7/2012 | Eisermann et al. | 623/17.14 |
| 8,277,508 B2* | 10/2012 | Trieu | 623/17.15 |
| 8,292,955 B2* | 10/2012 | Robinson et al. | 623/14.12 |
| 8,435,301 B2* | 5/2013 | Gerber et al. | 623/17.16 |
| 8,506,633 B2* | 8/2013 | Trieu | 623/17.12 |
| 8,551,172 B2* | 10/2013 | Park | 623/17.12 |
| 8,636,803 B2* | 1/2014 | Hibri et al. | 623/17.12 |
| 2002/0029080 A1* | 3/2002 | Mortier et al. | 623/2.36 |
| 2002/0045942 A1* | 4/2002 | Ham | 623/17.12 |
| 2002/0049498 A1* | 4/2002 | Yuksel et al. | 623/17.16 |
| 2002/0147496 A1* | 10/2002 | Belef et al. | 623/17.12 |
| 2002/0183848 A1* | 12/2002 | Ray et al. | 623/17.12 |
| 2003/0009224 A1* | 1/2003 | Kuras | 623/17.16 |
| 2003/0045939 A1* | 3/2003 | Casutt | 623/17.15 |
| 2003/0191534 A1* | 10/2003 | Viart et al. | 623/17.15 |
| 2003/0195628 A1* | 10/2003 | Bao et al. | 623/17.12 |
| 2003/0199982 A1* | 10/2003 | Bryan | 623/17.16 |
| 2004/0059416 A1* | 3/2004 | Murray et al. | 623/13.15 |
| 2004/0088047 A1* | 5/2004 | Spence et al. | 623/2.36 |
| 2004/0093082 A1* | 5/2004 | Ferree | 623/17.11 |
| 2004/0127982 A1* | 7/2004 | Machold et al. | 623/2.36 |
| 2004/0148026 A1* | 7/2004 | Bonutti | 623/16.11 |
| 2004/0236425 A1* | 11/2004 | Huang | 623/17.12 |
| 2004/0243238 A1* | 12/2004 | Arnin et al. | 623/17.12 |
| 2004/0249462 A1* | 12/2004 | Huang | 623/17.13 |
| 2004/0260396 A1* | 12/2004 | Ferree et al. | 623/17.12 |
| 2005/0004668 A1* | 1/2005 | Aklog et al. | 623/2.36 |
| 2005/0010297 A1* | 1/2005 | Watson et al. | 623/17.12 |
| 2005/0015150 A1* | 1/2005 | Lee | 623/17.12 |
| 2005/0027307 A1* | 2/2005 | Schwartz et al. | 606/151 |
| 2005/0033432 A1* | 2/2005 | Gordon et al. | 623/17.11 |
| 2005/0038509 A1* | 2/2005 | Ashe | 623/2.36 |
| 2005/0043804 A1* | 2/2005 | Gordon et al. | 623/17.16 |
| 2005/0090901 A1* | 4/2005 | Studer | 623/17.12 |
| 2005/0113923 A1* | 5/2005 | Acker et al. | 623/17.12 |
| 2005/0197702 A1* | 9/2005 | Coppes et al. | 623/17.12 |
| 2005/0197705 A1* | 9/2005 | Arnin et al. | 623/17.15 |
| 2005/0251259 A1* | 11/2005 | Suddaby | 623/17.12 |
| 2005/0267580 A1* | 12/2005 | Suddaby | 623/17.12 |
| 2006/0129240 A1* | 6/2006 | Lessar et al. | 623/17.14 |
| 2006/0195183 A1* | 8/2006 | Navia et al. | 623/2.18 |
| 2006/0241758 A1* | 10/2006 | Peterman et al. | 623/17.11 |
| 2006/0241765 A1* | 10/2006 | Burn et al. | 623/17.12 |
| 2006/0241766 A1* | 10/2006 | Felton et al. | 623/17.12 |
| 2006/0241778 A1* | 10/2006 | Ogilvie | 623/21.15 |
| 2006/0247780 A1* | 11/2006 | Bert | 623/17.16 |
| 2006/0293750 A1* | 12/2006 | Sherman et al. | 623/17.12 |
| 2006/0293751 A1* | 12/2006 | Lotz et al. | 623/17.12 |
| 2007/0038300 A1* | 2/2007 | Bao et al. | 623/17.12 |
| 2007/0038301 A1* | 2/2007 | Hudgins | 623/17.16 |
| 2007/0050020 A1* | 3/2007 | Spence | 623/2.11 |
| 2007/0050032 A1* | 3/2007 | Gittings et al. | 623/17.12 |
| 2007/0073402 A1* | 3/2007 | Vresilovic et al. | 623/17.12 |
| 2007/0135921 A1* | 6/2007 | Park | 623/17.12 |
| 2007/0135922 A1* | 6/2007 | Trieu | 623/17.12 |
| 2007/0148242 A1* | 6/2007 | Vilei et al. | 424/484 |
| 2007/0150060 A1* | 6/2007 | Trieu | 623/17.12 |
| 2007/0150061 A1* | 6/2007 | Trieu | 623/17.12 |
| 2007/0162137 A1* | 7/2007 | Kloss et al. | 623/17.15 |
| 2007/0168031 A1* | 7/2007 | Hudgins et al. | 623/17.12 |
| 2007/0173940 A1* | 7/2007 | Hestad et al. | 623/17.12 |
| 2007/0179607 A1* | 8/2007 | Hodorek et al. | 623/14.12 |
| 2007/0179608 A1* | 8/2007 | Ek et al. | 623/14.12 |
| 2007/0233258 A1* | 10/2007 | Hestad et al. | 623/17.12 |
| 2007/0233259 A1* | 10/2007 | Muhanna et al. | 623/17.12 |
| 2007/0260317 A1* | 11/2007 | Ankney et al. | 623/17.16 |
| 2007/0293947 A1* | 12/2007 | Mansmann | 623/14.12 |
| 2008/0033555 A1* | 2/2008 | Link et al. | 623/17.15 |
| 2008/0051889 A1* | 2/2008 | Hodorek | 623/14.12 |
| 2008/0065210 A1* | 3/2008 | McKay | 623/14.12 |
| 2008/0065216 A1* | 3/2008 | Hurlbert et al. | 623/17.13 |
| 2008/0086210 A1* | 4/2008 | Fox | 623/14.12 |
| 2008/0103607 A1* | 5/2008 | Krehl | 623/39 |
| 2008/0125860 A1* | 5/2008 | Webler et al. | 623/2.36 |
| 2008/0125863 A1* | 5/2008 | McKay | 623/11.11 |
| 2008/0132934 A1* | 6/2008 | Reiley et al. | 606/192 |
| 2008/0133008 A1* | 6/2008 | Truncale et al. | 623/14.12 |
| 2008/0234686 A1* | 9/2008 | Beaurain et al. | 606/90 |
| 2009/0030399 A1* | 1/2009 | Raiszadeh | 604/506 |
| 2009/0043389 A1* | 2/2009 | Vunjak-Novakovic et al. | 623/14.12 |
| 2009/0043398 A1* | 2/2009 | Yakimicki et al. | 623/23.51 |
| 2009/0069894 A1* | 3/2009 | Duggal et al. | 623/17.16 |
| 2009/0088846 A1* | 4/2009 | Myung et al. | 623/14.12 |
| 2009/0112323 A1* | 4/2009 | Hestad et al. | 623/17.12 |
| 2009/0222081 A1* | 9/2009 | Linder et al. | 623/2.1 |
| 2009/0222093 A1* | 9/2009 | Liu et al. | 623/17.12 |
| 2009/0222098 A1* | 9/2009 | Trieu et al. | 623/17.16 |
| 2009/0222099 A1* | 9/2009 | Liu et al. | 623/17.16 |
| 2009/0222103 A1* | 9/2009 | Fitz et al. | 623/18.11 |
| 2009/0248160 A1* | 10/2009 | Suddaby | 623/17.12 |
| 2009/0259314 A1* | 10/2009 | Linder-Ganz et al. | 623/14.12 |
| 2009/0264995 A1* | 10/2009 | Subramanian | 623/2.36 |
| 2009/0306778 A1* | 12/2009 | Marvel | 623/14.12 |
| 2010/0023126 A1* | 1/2010 | Grotz | 623/14.12 |
| 2010/0070032 A1* | 3/2010 | Park | 623/17.12 |
| 2010/0145454 A1* | 6/2010 | Hoffman | 623/17.12 |
| 2010/0152855 A1* | 6/2010 | Kuslich et al. | 623/17.12 |
| 2010/0262240 A1* | 10/2010 | Chavatte et al. | 623/17.11 |
| 2010/0268341 A1* | 10/2010 | Dvorak et al. | 623/17.12 |
| 2010/0280615 A1* | 11/2010 | Baumgartner et al. | 623/17.12 |
| 2010/0292798 A1* | 11/2010 | Maestretti | 623/17.12 |
| 2011/0098816 A1* | 4/2011 | Jacob et al. | 623/17.11 |
| 2011/0144757 A1* | 6/2011 | Linares | 623/18.11 |
| 2011/0172768 A1* | 7/2011 | Cragg et al. | 623/14.12 |
| 2011/0224791 A1* | 9/2011 | Hodorek et al. | 623/14.12 |
| 2011/0224801 A1* | 9/2011 | Mansmann | 623/23.72 |
| 2011/0238180 A1* | 9/2011 | Fritz et al. | 623/14.12 |
| 2011/0288642 A1* | 11/2011 | Forsell | 623/14.12 |
| 2011/0319996 A1* | 12/2011 | Barrall | 623/17.12 |
| 2012/0010713 A1* | 1/2012 | O'Halloran et al. | 623/17.12 |
| 2012/0022649 A1* | 1/2012 | Robinson et al. | 623/17.12 |
| 2012/0165941 A1* | 6/2012 | Rabiner et al. | 623/17.12 |
| 2012/0179247 A1* | 7/2012 | Navia | 623/2.37 |
| 2012/0265304 A1* | 10/2012 | Mayer | 623/17.12 |
| 2012/0316645 A1* | 12/2012 | Grotz | 623/14.13 |
| 2013/0123922 A1* | 5/2013 | McCormack | 623/17.12 |
| 2013/0131806 A1* | 5/2013 | Carpenter | 623/17.12 |
| 2013/0282121 A1* | 10/2013 | Prewett | 623/17.12 |
| 2013/0289725 A1* | 10/2013 | Donovan et al. | 623/17.12 |
| 2013/0297025 A1* | 11/2013 | Wardlaw | 623/17.12 |
| 2014/0031926 A1* | 1/2014 | Kudlik et al. | 623/2.11 |

* cited by examiner

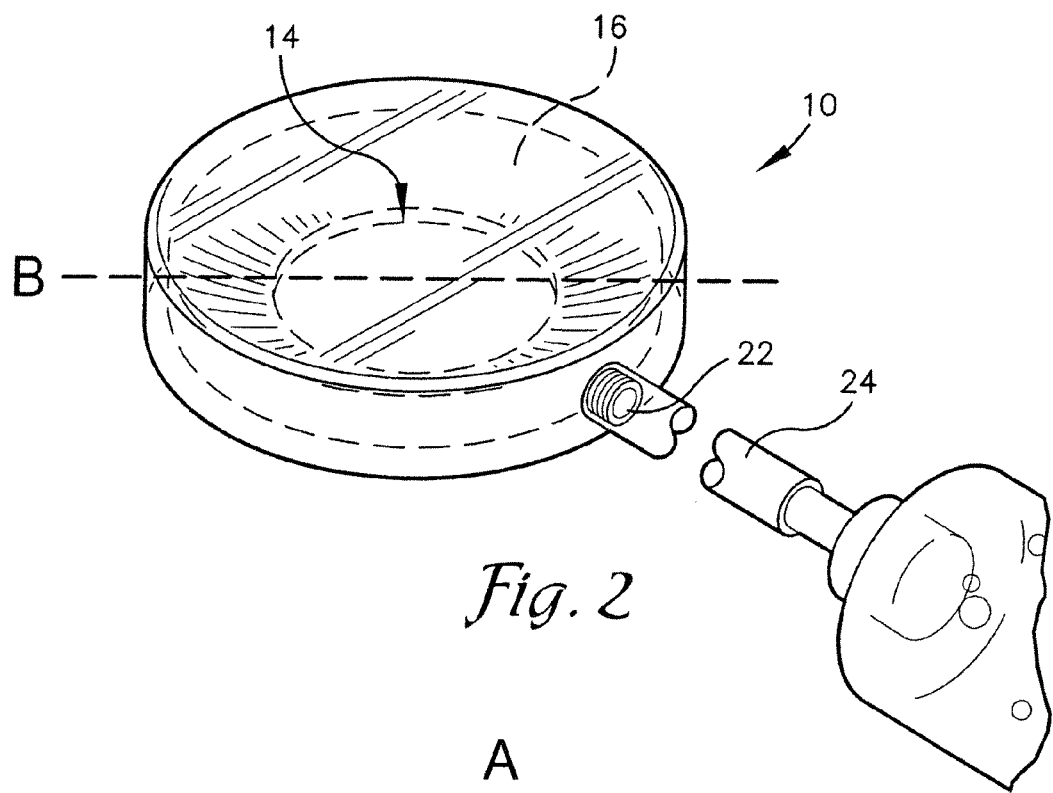
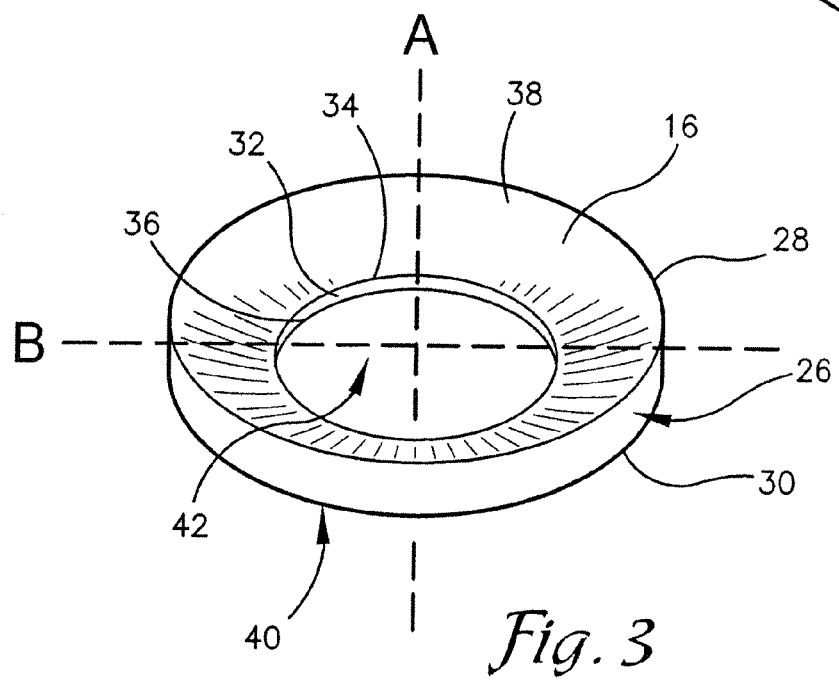

BUFFER FOR A HUMAN JOINT AND METHOD OF ARTHROSCOPICALLY INSERTING

RELATED APPLICATION

This patent application claims priority to and is a continuation of U.S. Pat. No. 7,976,578, issued Jul. 12, 2011, and entitled "Buffer for a Human Joint and Method of Arthroscopically Inserting," which is hereby incorporated by reference in its entirety.

BACKGROUND

1. Field

Embodiments of the present invention relate to apparatus and methods of providing a buffer for a human joint so as to prevent painful bone on bone contact. More particularly, embodiments of the present invention present a buffer for insertion between the femur and tibia in the human knee, so as to protect worn or damaged articular cartilage or exposed bone and to allow the articular surfaces remaining on the femur and tibia to continue to move against each other less painfully.

2. Description of the Related Art

The human knee joint is one of the most complex joints of the body and is also highly susceptible to damage because it is a weight bearing joint. The knee joint itself is comprised of the femur (thigh bone), the tibia (shin bone), the patella (kneecap), articular cartilage, and menisci, which are a type of crescent-shaped cartilage that lies between the femur and tibia. The menisci are located in the medial and lateral articulations of the knee and sometimes act as shock-absorbing pads. The knee is also compromised of tissues that are muscle, ligament, the lining tissue (synovium), and the synovial fluid which is secreted by the synovium.

The ends of the femur and tibia are coated with articular cartilage, which is smooth and hard, so as to provide the femur, tibia, and patella with a slick surface during normal movement. The articular cartilage has a very low coefficient of friction and can also receive large compressive loads, which makes it vital to ensure ease of movement of the knee joint and prevent bone on bone contact between the femur and tibia. Normal articular cartilage is about 50 times slicker than ice.

Over time, the articular cartilage on the femur and tibia, and in any other human joint, wears and degenerates, such that it thins or in some joints is completely lost. Upon wear of the articular cartilage, the slick, low friction surfaces from the cartilage are lost, and the ends of the femur and tibia banes are exposed. Without any protecting articular cartilage, the femur and tibia contact each. This bone on bone contact is painful, and is often the end result of osteoarthritis. Additionally, bones can also become hard and sclerotic over time with associated loss of articular cartilage, which can further increases the pain.

Many methods have been developed to either replace worn cartilage or otherwise minimize the pain associated with the loss of the articular cartilage. The methods have all had varying degrees of success but are often accompanied by very extensive and invasive surgery. All invasive methods are costly, often requiring implanting nonbiologic parts within the knee, or, in some instances, human cadaver parts. These methods of treatment also require lengthy rehabilitation, which often times leaves the patient in considerable pain.

One method of treatment that has been used is implantation of cadaver menisci. This method has had only limited success and multiple failures. A second method is chondroplasty, or removal of and thinning out the existing damaged cartilage. This method is used to smooth the cartilage to reduce the friction between the femur and tibia, and remove the flaps of cartilage that have delaminated from the bone. The success of this procedure is limited by the amount of cartilage remaining, and doctors guard against removal of too much of the articular cartilage so as to prevent exposure of the subchondral bone. For older patients or patients with traumatic arthritis of their knees, chondroplasty has only limited application because of the lack of healthy articular cartilage.

If the articular cartilage loss is small, an osteochondral autograft transplant (known as an OATS procedure) can be performed. The OATS procedure requires removing a dowel shaped portion of bone and replacing it with a commensurate dowel shaped portion of articular cartilage from another area of the knee, another joint, or even a cadaver. The OATS procedure is relatively invasive, has a fairly lengthy rehabilitation time, and has also only had limited success.

An even further alternative to repairing articular cartilage damage is growing the patient's own cartilage in tissue cultures and placing the newly grown cartilage in the areas of cartilage loss. This is an expensive and often unsuccessful method of treatment.

In the most extreme of cases of arthritis, the knee joint may be artificially resurfaced or even replaced. In artificial joint replacement, the ends of the femur and tibia are capped with plastic or metal pieces that are cemented to the ends of the bone. Alternatively, the ends of the femur and tibia can be replaced with a biologic ingrowth coating of the metal used, which removes the need for the cement. This procedure is presently the standard approach to treating severe osteoarthritis of the knee; however, the risks from this procedure are numerous, and this is particularly unfortunate for patients who can ill afford a major complication from this extensive surgery. In places where these artificial joints have been inserted, wear eventually occurs in the polyethylene surface between the metal caps, which can lead to bone destruction just from the particles of the polyethylene. Moreover, this procedure is not only quite invasive but requires a lengthy rehabilitation time. Thus, for these reasons, many doctors delay as long as possible this invasive procedure in many patients.

An even further method of treatment is arthrosporic debridement, which is much less invasive but almost always unsuccessful in limiting the pain from the damaged joint surface, unless most of the pain is from a torn cartilage or loose body in the joint that can be removed arthroscopically.

The problems associated with each of the above procedures are highly dependant on the age and medical condition of the patient. For older patients, their ability and desire to engage in an invasive procedure that requires lengthy rehabilitation is often limited. Moreover, for older patients who are not necessarily engaging in many activities or who do not require a long-term solution to adjust their pain and discomfort, having an invasive, complicated procedure performed is not ideal.

Accordingly, there is a need for a less risky and improved apparatus and method for alleviating and addressing pain resulting from a loss of articular cartilage. There is a need for a new apparatus and method of treatment of lost cartilage that extends beyond attempting to fix or replace damaged cartilage, but instead provides an apparatus and method of treatment that is minimally invasive, relatively inexpensive, requires relatively short rehabilitation time, and is suitable for older patients. This invention solves many of the above-described problems and provides a distinct advantage in the art of medical treatment for prevention of bone on bone contact due to the loss of articular cartilage. More particularly this invention provides a new apparatus and method of treatment to address the pain and discomfort associated with the loss of articular cartilage by interposing a thin but slick barrier between the tibia and femur. This invention provides a buffer between the femur and tibia in the human knee that does not require suturing or other permanent securement to muscles, ligaments, or tendons in the knee.

SUMMARY

The present invention solves the above-described problems and provides a distinct advance in the art of medical treatments for prevention of bone-on-bone contact due to the loss of articular cartilage. More particularly, the present invention provides a new method of treatment to address the pain and discomfort associated with the loss of articular cartilage. In particular, embodiments of the present invention provide a buffer independently held between a human's femur and tibia and that does not require suturing or other permanent securement to any muscle, ligament, or tendon in the knee.

The buffer of embodiments of the present invention comprises an outer sack formed of a pliable material and having a one-way valve; a generally circularly-shaped, rigid inner ring within the outer sack, the inner ring having a top surface and a bottom surface angled inwardly with respect to each other, such that the ring is generally concave; and a friction reducing fluid received within the outer sack via the one-way valve.

The buffer is inserted into the knee joint using a specially designed sleeve comprising a body and a stylus or plunger. The body is generally an ovoid hollow tube into which is inserted the buffer. The stylus or plunger includes a fluid line comprising a tube through which a fluid can be pumped. The fluid line and buffer, when received within the sleeve, are in fluid communication, such that the fluid can be inserted into the outer sack of the buffer once the buffer is positioned in the knee joint.

To insert the buffer into the sleeve, the buffer is compressed into the sleeve, and the stylus is screwed or otherwise secured to the rigid inner ring of the buffer. The stylus is then unscrewed from the buffer once the device is positioned in the knee joint and after the fluid is placed into the buffer via a one way valve in the buffer.

A method of inserting the buffer into the knee comprises the steps of providing the buffer, providing a sleeve having a stylus operable to securely receive the buffer during insertion, and injecting fluid into the outer sack during insertion via the one way valve located in the buffer. To insert the buffer in the sleeve, the buffer is compressed side to side, placed into the sleeve, and removably secured to the stylus. After being placed into the knee, the buffer is then injected with fluid to help the surfaces of the buffer move over each other by reducing friction between them. Once the buffer is injected with this fluid, the stylus is unscrewed form the rigid inner ring, the fluid is held in place by the one way valve, the sleeve is removed, the skin is closed, and the operation is complete.

BRIEF DESCRIPTION OF THE DRAWINGS

Embodiments of the present invention are described in detail below with reference to the attached drawing figures, wherein:

FIG. 2 is a perspective view of a buffer of the present invention comprising an outer sack and an inner ring;

FIG. 3 is a perspective view of the inner ring of the buffer of the present invention.

Figure 1:
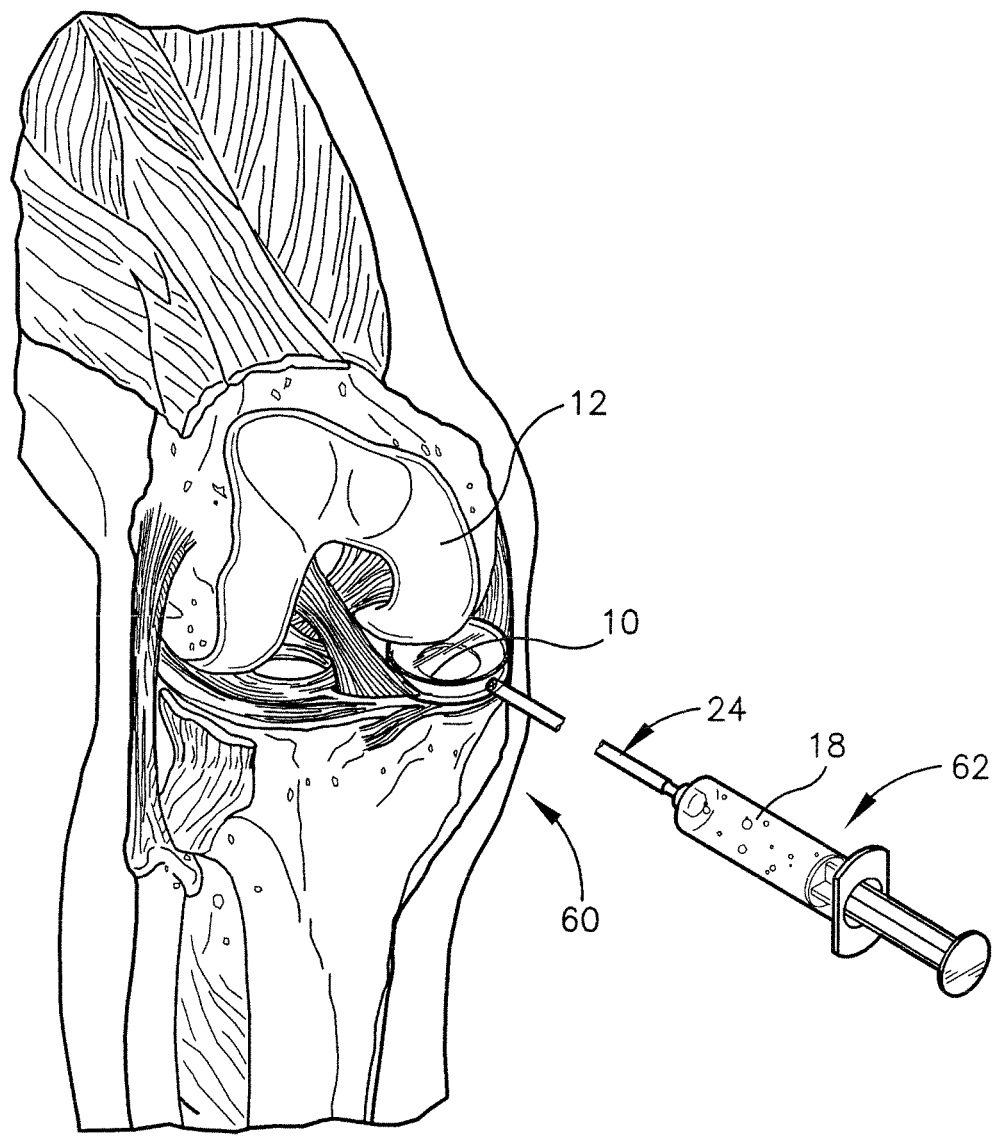
FIG. 1 is a perspective view of a human knee showing the skin removed and illustrating the femur, tibia, articular cartilage covering ends of the femur and tibia, and menisci.

The drawing figures do not limit the present invention to the specific embodiments disclosed and described herein. The drawings are not necessarily to scale, emphasis instead being placed upon clearly illustrating the principles of the invention.

DETAILED DESCRIPTION

Turning now to the drawing figures, and particularly FIG. 1, a buffer 10 for a human joint constructed in accordance with embodiments of the invention is illustrated. The buffer 10 is configured to be inserted into any human joint that is a bearing surface, such as the glenohumeral joint (shoulder joint) or the knee joint. Embodiments of the present invention will be discussed with respect to the knee joint, although it is to be understood that the invention is equally applicable to other joints.

The buffer 10 is configured to be inserted into a patient's knee in the space between the patient's femur and tibia and is intended to supplement any remaining articular cartilage 12 in the joint, or, in the instances where there is no remaining articular cartilage 12, provide a complete buffer between the femur and tibia. The buffer 10 is further sized so that it does not interfere with the menisci of the patient's knee, as illustrated in FIG. 1.

The buffer 10 of an embodiment of the present invention comprises an outer sack 14 enclosing an inner ring 16 and further configured to receive a friction reducing fluid 18, as illustrated in FIGS. 1 and 2. As described in more detail below, the buffer 10 may be arthroscopically inserted into the patient's knee using a sleeve 20, illustrated in FIG. 4, especially designed for stable securement of the buffer 10 during the arthroscopic procedure.

The outer sack 14 of the buffer 10 is generally circular in shape, although the sack 14 may also be generally oval in shape while being inserted into the knee through the sleeve 20. The sack 14 is preferably approximately 10-50 mm in size, and more preferably approximately 30-60 mm, and most preferably approximately 35-45 mm. In an average patient, the space between the femur and tibia with an average amount of articular cartilage can be opened to 10-15 mm at arthroscopy but contract to 0 mm when the stress on the ligament is relaxed. The sack 14 having the inner ring 16 located therein has a height that is preferably at least the distance between the femur and tibia, i.e., approximately 10 mm, and is flexible. More preferably, the sack's height is slightly larger than the distance between the femur and tibia, such that the height of the sack 14 is approximately the same height as the inner ring. In embodiments of the invention, the buffer, including the inner ring, are manufactured in various sizes to accommodate differently-sized knee joints.

The sack 14 is preferably formed of a material that will be accepted by a human body and that is durable. Because of the pressure that the sack 14 will receive due to the contraction and movement of the femur and tibia, the sack 14 is further preferably formed of a pliable, resilient material. The material is also impermeable, such that the friction reducing fluid 18 does not escape from the sack 14. An exemplary material includes polyethylene, although any material having the above-described properties will suffice. The material forming the sack 14 may be translucent, as illustrated in FIG. 2, or opaque.

The sack 14 includes a one-way valve 22 that is fluidly connected to a hollow fluid line 24, as illustrated in FIGS. 1 and 2. The hollow fluid line 24 allows for passage of the fluid 18 therethrough. The friction reducing fluid 18, described in more detail below, is inserted into the sack 14 after the buffer 10 is positioned inside the patient's knee. The fluid 18 is inserted into the sack 14 via the fluid line 24, which will be of a length sufficiently long to allow insertion of the fluid 18 into the sack 14 via the sleeve 20 or other instrument, as also described in more detail below. The valve 22 preferably includes threads 23 (not shown) After the fluid 18 is inserted into the sack 14, the fluid line 24 is preferably unscrewed. Alternatively, the line 24 may be cut proximal to the sack 14 or otherwise formed so that it can be removed from the sack 14. The one-way valve 22 allows receipt of the friction reducing fluid 18 via the filler line 24 and after the buffer 10 is inserted into the patient's knee. The valve 22 is one-way, however, so that it does not allow for escape of the fluid 18 via the valve 22.

The friction reducing fluid 18 is any fluid that is accepted by a human body and that assists in allowing ease of movement of the inner ring 16 within the outer sack 14. Exemplary friction reducing fluids 18 include the patient's own synovial fluid found in synovial joints, such as the knee joint, and artificial fluids, such as SYNVISC®, manufactured by Genzyme Corporation.

The inner ring 16 is generally circular in shape, although the ring 16 may also be generally oval in shape. During insertion, the inner ring is flexed to be oval in shape. The inner ring 16 is preferably approximately 20-60 mm in circumference, and more preferably approximately 25-55 mm, and most preferably approximately 27.5-32.5 mm. The inner ring 16 is manufactured therefore to fit within the sack 14. In preferred form, the inner ring 16 and sack 14 are manufactured as a unit, such that the inner ring 16 is located within the sack 14 and sold as single unit. As noted above, the sack and inner ring may be manufactured in various sizes to fit each particular patient.

The inner ring 16 is preferably solid and formed of a resiliently rigid material, such that the ring 16 can withstand, with little or no deformation along a longitudinal axis A, a relatively high degree of loading pressure occurring from placement between the femur and tibia, yet can also be flexed or otherwise deformed along a transverse axis B for ease of placement within the patient's knee. In particular, during insertion in the knee joint, the ring 16 can be compressed side to side along axis B for placement in the sleeve. However, the ring's 16 resiliently rigid material allows it to return to its generally circular shape once the pressure along the axis B is removed and the buffer is placed between the tibia and femur.

The ring 16 preferably comprises an outer surface 26 having a top edge 28 and a bottom edge 30, an inner surface 32 having a top edge 34 and a bottom edge 36, a top surface 38, and a bottom surface 40. The outer, inner, top, and bottom surfaces 26,32,38,40 are preferably integrally formed and together define a hollow interior 42 of the ring 16. The top and bottom surfaces 38,40 are angled inwardly with respect to each other, such that the top surface 38 extends downwardly from the top edge 28 of the outer surface 26 and to the top edge 34 of the inner surface 32, and similarly, the bottom surface 40 extends upwardly (not shown) from the bottom edge 30 of the outer surface 26 and up to the bottom edge 36 of the inner surface 32. In this manner, the top and bottom surfaces 38,40 form the ring 16 that is generally concave when viewed from a top of the ring 16 and flat when viewed from a bottom of the ring 16. This further provides a ring wherein a height of the ring along an outer diameter is larger than a height of the ring along an inner diameter, as illustrated in FIG. 3.

The concavity of the ring 16 and the orientation of the top and bottom surfaces 38,40 forms a generally V-shaped cross-section of the ring 16 when cut along the longitudinal axis A. The concavity assists with placement and retention of the buffer 10 between the patient's femur and tibia in the patient's knee. In particular, the buffer 10 is partially held in place within the patient's knee and between the femur and tibia by the load-bearing pressure that naturally occurs from the muscles, ligaments, and bones in the patient's knee and the weight of the body. However, to insure that the buffer 10 does not drift outside its proper placement when the knee is not exhibiting load-bearing pressure, the concave top and bottom surfaces 38,40 of the inner ring 16 assist in locating the buffer 10 between the femur and tibia.

Figure 4:
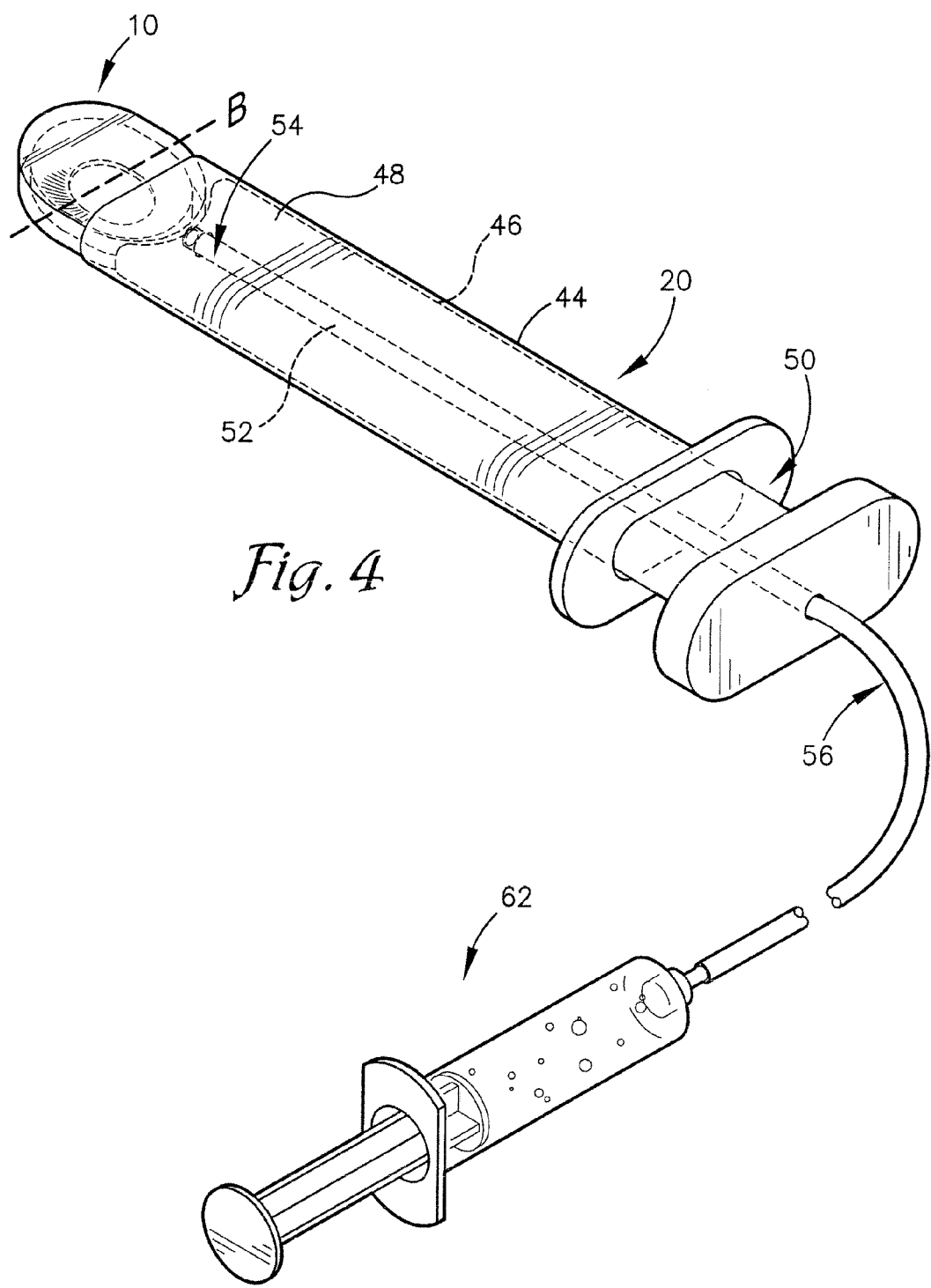
FIG. 4 is a perspective view of the buffer of the present invention received within a sleeve designed for arthroscopically inserting the buffer into a patient's knee.

As illustrated in FIG. 4, the sleeve 20 used to insert the buffer 10 into the knee comprises a generally ovoid, hollow body 44, a stylus or telescoping plunger 46 (not necessarily drawn to scale with respect to length in FIG. 4) having proximal and distal ends 48,50 and at least partially housed within the body 44, and the fluid line 24 having proximal and distal ends 54,56, partially housed within the body 44 and 46, and operable to allow the passage of fluid therethrough. The body 44 of the sleeve 20 is generally ovoid to accommodate the shape of the buffer 10 upon insertion, as described in more detail below. The fluid line 24 is passed through the plunger 46 and is screwed onto and fluidly connected with the valve 22 of the sack 14 at the proximal end 54 of the line 24 and with a fluid source (not shown) at the distal end 56 of the line 24.

The plunger 46 includes a curved neck 58 located at the proximal end 48 and operable to support the buffer 10 during placement in the patient's knee. The buffer 10 is preferably flexed along the transverse axis B into a generally ovoid shape so as to be partially inserted into the hollow body 44 of the sleeve 20, as illustrated in FIG. 4. The buffer 10 is inserted into the body 44 such that the valve 22 of the buffer 10 is screwed into fluid communication with the fluid line 24. Additionally, during insertion the buffer is supported by the curved neck 58 of the plunger 46.

The buffer 10 is preferably arthroscopically inserted into the patient's knee using the sleeve 20. The buffer 10 is flexed into the generally ovoid shape illustrated in FIG. 1 and then positioned within the sleeve 20. Flexing the buffer 10 into the ovoid shape facilitates insertion into the knee joint. The buffer 10 is held into place during insertion by being supported by the neck 58. Alternatively, the neck 58 could include further structure (not shown) for supporting and holding the buffer 10 at least partially in the sleeve 20 during insertion, such as a U-shaped arm that receives the buffer 10.

As discussed briefly above and as illustrated in FIG. 1, the buffer 10 is inserted between the tibia and femur of the knee joint. The buffer 10 can be inserted on either side of the knee, as illustrated in FIG. 1.

As noted above, upon insertion, the buffer 10 is flexed into the ovoid shape. Once the buffer 10 is released from the sleeve 20, it springs back into its generally circular shape, as illustrated in FIG. 1. Once inserted, the friction reducing fluid 18 is then inserted into the buffer 10 via the fluid line 24, which is fluidly connected between the one way valve 22 of the buffer 10 and the sleeve 20. Alternatively, the fluid 18 may be inserted into the buffer 10 prior to placement between the femur and tibia and/or prior to release from the sleeve 20. As noted above, after the fluid is inserted into the sack 14, the fluid line 24 is preferably physically separated from the buffer, so as to not be an irritant to the patient, by either cutting the line 24 proximal to the sack 14 or otherwise forming the line 24 so that it can be removed from the sack 14.

Once inserted, the rigidity of the inner ring 16 of the buffer 10 acts to keep the femur and tibia separated, such that the two bones are not contacting each other. Additionally, as noted above, once inserted, the load-bearing pressure of the femur and tibia assist in locating and holding the buffer in place between the bones. The concavity of the top and bottom surfaces 38,40 of the ring 16 further assists in holding the buffer 10 in place, especially when there is no load-bearing pressure exhibited between the femur and tibia. The friction reducing fluid 18 then assists in movement of the femur and tibia against the buffer 10 and in particular, the inner ring 16 of the buffer 10.

The buffer 10 is advantageously independently held within the knee joint and does not have to be sutured to any muscle, ligament, or tendon. Moreover, the buffer 10 can be used with any amount of articular cartilage 12 and menisci, such that it is not limited to being only used with very little cartilage. Although the buffer of embodiments of the present invention are preferably permanent, it is to be understood that with time, the buffer 10 may become sufficiently worn so as to require replacement. However, such will likely not be the norm, and the buffer 10 is expected to last many years, depending on the activity level, weight, and age of the patient and other common degradation factors.

Although the invention has been described with reference to the preferred embodiment illustrated in the attached drawing figures, it is noted that equivalents may be employed and substitutions made herein without departing from the scope of the invention as recited in the claims. For example, the sleeve 20 could not include the fluid line 24, such that the friction reducing fluid 18 is inserted via a separate line and a syringe 62, as illustrated in FIG. 1.

Having thus described the preferred embodiment of the invention, what is claimed as new and desired to be protected by Letters Patent includes the following:

The invention claimed is:

1. An apparatus comprising:
    a pliable and resilient sack; and
    a reinforcement structure housed within the sack, the reinforcement structure having top and bottom surfaces with common inner and outer perimeters and being independently movable within and with respect to the sack,
        wherein at least one of the top and bottom surfaces of the reinforcement structure is angled with respect to the other surface, such that at least one of the top and bottom surfaces extends towards the other surface from the outer perimeter and to the inner perimeter,
    said apparatus configured for insertion between two bones of a human body so as to at least partially prevent the bones from contacting each other; and wherein the sack completely covers the top and/or the bottom surfaces of the reinforcement structure.

2. The apparatus of claim 1, wherein the reinforcement structure is a generally circular or oval-shaped ring received within the sack.

3. The apparatus of claim 1, wherein the inner perimeter of the reinforcement structure is an annular inner wall, and the outer perimeter of the reinforcement structure is an annular outer wall.

4. The apparatus of claim 1, wherein the inner perimeter of the reinforcement structure defines a hollow interior.

5. The apparatus of claim 1, wherein a fluid receiver is mounted on the sack.

6. The apparatus of claim 5, wherein the receiver includes an engagement structure operable to securely mate with a fluid-delivery device.

7. The apparatus of claim 6, wherein the engagement structure is an external thread.

8. The apparatus of claim 5, wherein the receiver includes a one-way valve operable to receive and retain fluid within the sack.

9. A buffer for placement between a human's femur and tibia, the buffer comprising:
    a pliable and resilient sack; and
    a ring housed within the sack, the ring having upper and lower surfaces, an outer diameter, and an inner diameter and being independently movable within and with respect to the sack,
        wherein the inner diameter is less than the outer diameter,
        wherein the ring is operable to (i) deform along a first axis that is generally parallel to the upper and lower surfaces when subjected to pressure, and (ii) substantially resist deformation along a second axis that is generally perpendicular to the first axis when subjected to pressure,
        wherein said buffer is configured for insertion between the femur and tibia so as to at least partially prevent the bones from contacting each other; and wherein the sack completely covers the upper and/or the lower surfaces of the ring.

10. The buffer of claim 9, wherein the sack occupies a volume and includes a cavity configurable to be filled with a fluid, the sack being configurable to substantially conform to the ring to decrease the volume when the cavity is not filled with the fluid.

11. The buffer of claim 9, further comprising: a regulator on the sack operable to permit upper and lower surfaces of the sack to be increasingly spaced from each other.

12. The buffer of claim 11, wherein the regulator is a one-way valve for receipt of a friction reducing fluid into the sack to define a space between the upper and lower surfaces of the sack.

13. A buffer for placement between a human's femur and tibia, the buffer comprising:
    a pliable and resilient sack;
    a ring housed within the sack, the ring having upper and lower surfaces, an outer diameter, and an inner diameter and being independently movable within and with respect to the sack; and
    a fluid receiver including an engagement structure operable to securely mate with a fluid-delivery device, the fluid receiver being mounted on the sack,
        wherein the inner diameter is less than the outer diameter,
        wherein the ring is operable to (i) deform along a first axis that is generally parallel to the upper and lower surfaces when subjected to pressure, and (ii) substantially resist deformation along a second axis that is generally perpendicular to the first axis when subjected to pressure,
        wherein said sack occupies a volume and includes a cavity configurable to be filled with a fluid, the sack being configurable to substantially conform to the ring to decrease the volume when the cavity is not filled with the fluid,
        wherein said buffer is configured for insertion between the femur and tibia so as to at least partially prevent the bones from contacting each other, and wherein the fluid receiver includes a one-way valve operable to receive and retain fluid within the sack.

* * * * *